United States Patent
Heismann

(10) Patent No.: US 7,050,530 B2
(45) Date of Patent: May 23, 2006

(54) METHOD AND APPARATUS FOR THE SPATIALLY-RESOLVED DETERMINATION OF THE ELEMENT CONCENTRATIONS IN OBJECTS TO BE EXAMINED

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/983,061

(22) Filed: Nov. 5, 2004

(65) Prior Publication Data

US 2005/0100125 A1    May 12, 2005

(30) Foreign Application Priority Data

Nov. 7, 2003    (DE) ................ 103 52 013

(51) Int. Cl.
*G01N 21/00*    (2006.01)

(52) U.S. Cl. ............................ 378/5; 378/53
(58) Field of Classification Search ............... 378/5, 378/4, 57, 53, 54, 55, 56
See application file for complete search history.

(56) References Cited

U.S. PATENT DOCUMENTS 4,247,774 A    1/1981    Brooks
6,320,931 B1*    11/2001    Arnold ................ 378/56
6,836,528 B1*    12/2004    Reddy et al. ........... 378/5

FOREIGN PATENT DOCUMENTS

DE    101 43 131 A1    4/2003

* cited by examiner

*Primary Examiner*—David V. Bruce
*Assistant Examiner*—Hoon Song
(74) *Attorney, Agent, or Firm*—Harness, Dickey & Pierce, PLC

(57) ABSTRACT

A method is proposed for the spatially-resolved determination of the concentration of n elements and/or element combinations in an object to be examined that includes these elements and/or element combinations. In the method, use is made of an X-ray installation to record a number of digital X-ray images of at least one region of the object to be examined with the aid of $m \geq n$ different spectral distributions of the X-radiation $S(E)$ and/or of the detector sensitivity $D(E)$, in order to obtain m attenuation values for each pixel representing the same location in the X-ray images. The concentrations of the n elements and/or element combinations are then calculated for at least one pixel from the respective m attenuation values while taking account of known spectral absorption spectra of the n elements and/or element combinations and of the m different spectral distributions of the X-radiation and/or of the detector sensitivity.

18 Claims, 2 Drawing Sheets

METHOD AND APPARATUS FOR THE SPATIALLY-RESOLVED DETERMINATION OF THE ELEMENT CONCENTRATIONS IN OBJECTS TO BE EXAMINED

The present application hereby claims priority under 35 U.S.C. §119 on German patent application number DE 10352013.9 filed Nov. 7, 2003, the entire contents of which are hereby incorporated herein by reference.

FIELD OF THE INVENTION

The present invention generally relates to a method and to an apparatus for the spatially-resolved determination of the concentrations of elements and/or element combinations in an object to be examined that includes the elements and/or element combinations, with the aid of an X-ray absorption technique.

BACKGROUND OF THE INVENTION

The result of radiographic methods such as, for example, computed tomography (CT), mammography, an giography, X-ray inspection technology or comparable methods is firstly the representation of the attenuation of an X-ray beam along its path from the X-ray source to the X-ray detector in a projection image. This attenuation is caused by the transradiated materials along the beam path. Thus, the attenuation can also be understood as the line integral over the attenuation coefficients of all volume elements (voxels) along the beam path.

Particularly in the case of tomography methods, for example in the case of X-ray computer tomography, it is possible to use the reconstruction methods to calculate back from the projected attenuation data to the attenuation coefficients $\mu$ of the individual voxels. Thus, one can arrive at a substantially more sensitive examination than in the case of purely considering projection images.

Instead of the attenuation coefficient, a value normalized to the attenuation coefficient of water, the so-called CT number, is generally used to represent the attenuation distribution. This number is calculated from an attenuation coefficient $\mu$ currently being determined by measurement, and the reference attenuation coefficient $\mu_{H2O}$, according to the following equation:

$$C = 1000 \times \frac{\mu - \mu_{H2O}}{\mu_{H2O}} [HU],$$

where the CT number C is expressed using the Hounsfield unit [HU]. A value of $C_{H2O}=0$ HU results for water, and a value of $C_L=-1000$ HU for air. Since both representations can be transformed into one another, or are equivalent, the generally selected term of attenuation value or attenuation coefficient denotes both the attenuation coefficient $\mu$ and the CT value in what follows.

However, it is not possible to use the attenuation value of an X-ray picture to deduce the material composition of an object, since the X-ray absorption is determined both by the effective atomic number of the material and by the material density. Materials and/or tissues of different chemical and physical composition can therefore exhibit identical attenuation values in the X-ray image.

In order to improve the informativeness of an X-ray image based on the local attenuation coefficients, it is therefore known from U.S. Pat. No. 4,247,774 A, for example, to use mutually differing X-ray spectra or X-ray quantum energies in order to produce an X-ray image. This method, used in the field of computer tomography, which is also generally denoted as two-spectra CT, utilizes the fact that materials of higher atomic number absorb low-energy X-radiation substantially more intensely than do materials of lower atomic number. By contrast, in the case of higher x-radiation energies the attenuation values become assimilated and are largely a function of the material density. By calculating the differences in the X-ray images recorded with different X-ray tube voltages, it is therefore possible to obtain additional information relating to the materials on which the individual image regions are based.

Yet more specific items of information are obtained when, in addition, the method of so-called base material decomposition is applied to X-ray images. In this method the X-ray attenuation values of an object to be examined are measured with the aid of X-ray beams of lower and higher energy, and the values obtained are compared with the corresponding reference values of two base materials such as, for example, calcium for skeletal material and water for soft part tissues. It is assumed here that each measured value can be represented as a linear superposition of the measured values of the two base materials. Thus, a skeletal component and a soft tissue component can be calculated for each element of the pictorial display of the object to be examined from the comparison with the values of the base materials, thus enabling a transformation of the original pictures into displays of the two base materials.

German patent application DE 101 43 131 A1 further discloses a method whose sensitivity and informativeness further exceeds the base material decomposition and, for example, enables a functional CT imaging of high informativeness. The method can be used to calculate the spatial distribution of the density $\rho$ (r) and the effective atomic number Z (r) by evaluating spectrally influenced measured data of an X-ray apparatus. Body constituents such as, for example, iodine or the like can be determined quantitatively from a combined evaluation of the distribution of the density and effective atomic number and, for example, instances of calcification can be removed by segmentation on the basis of the atomic number.

However, none of the methods represented so far permit the concentration of elements and/or element combinations of which the object to be examined is composed to be determined in a spatially resolved fashion.

SUMMARY OF THE INVENTION

It is therefore the object of an embodiment of the present invention to specify a method and an apparatus for the spatially-resolved determination of the concentrations of elements and/or element combinations in an object to be examined that includes these elements and/or element combinations.

In one embodiment, in the present method for spatially-resolved determination of the concentrations of n elements and/or element combinations in an object to be examined that includes the n elements and/or element combinations, use is made of an X-ray installation to record simultaneously or sequentially under the same geometric conditions a number of digital X-ray images of at least one region of the object to be examined with the aid of m≧n different spectral distributions of the X-radiation S(E) and/or of the detector sensitivity D(E), in order to obtain m attenuation values μi (i=1, ... m) for each forming element (pixel) representing the same location in the X-ray images. Subsequently, the concentrations $c_j$ of the n elements and/or element combinations are calculated for one or more pixels from the respective m attenuation values μi while taking account of known spectral absorption spectra $K_j(E)$ (j=1 . . . n) of the n elements and/or element combinations and of the m different spectral distributions of the X-radiation S(E) and/or of the detector sensitivity D(E).

It follows that the spectral apparatus function, that is to say a combination of the X-ray spectrum S(E) and the detector sensitivity D(E) of the X-ray installation, must be known for each of the spectral distributions in order to carry out the method. The spectral distribution of the X-radiation S(E) is generally a function in this case of the type of the X-ray tube used, as well as of the tube voltage and, if appropriate, filters additionally used. The detector sensitivity D(E) is a property of the X-ray detectors used, which convert different spectral components of a radiation with different efficiencies, and therefore weight them differently. These installation-specific variables can be determined once directly or indirectly by way of the attenuation values of calibration samples. Of course, it is also possible to derive these functions from appropriate data, characterizing the tube type and the detector type, of the technical specifications of the X-ray installation.

The plurality of digital X-ray images need not necessarily be recorded sequentially, for example, as recordings using the different tube voltage. Since each X-ray tube emits an X-ray spectrum with a certain width, it is also possible given an appropriate spectrally selective configuration of the associated detector unit for various X-ray images to be recorded simultaneously as far as possible or completely. It is possible for this purpose to make use of a plurality of X-ray detector arrays that are separately present, for example.

In a preferred refinement, use is made of X-ray detectors that are selective in terms of quantum energy and supply attenuation values resolved in accordance with different spectral regions. The X-ray detectors in this case measure different spectral regions, that is to say different energy regions of the X-radiation. It is preferred for this purpose to undertake a uniform subdivision of the primary energy spectrum, that is to say, for example, in intervals of 30–40 keV, 40–50 keV, . . . 130–140 keV, in the case of a primary energy spectrum including 30–140 keV.

By recording this plurality of digital X-ray images of the region of interest of the object to be examined, and doing so under in each case the same geometric conditions, different attenuation values $\mu_i$ (i=1 . . . m) are obtained as a rule for each of the pixels, representing the same location, of the X-ray images m. It is then possible for at least one of these pixels to calculate the concentrations $c_j$ (j=1 . . . n) of the n elements and/or element combinations from the respectively m absorption or attenuation values assigned to this pixel, taking account of the m different spectral distributions that are represented by the spectral apparatus functions, and taking account of the known spectral absorption spectra $\kappa_j(E)$ of the n element and/or element combinations. Use is made for this purpose of the fact that the measured attenuation values depend only on these concentrations and the apparatus functions known or determined in advance. The spectral absorption spectra κ(E) of the individual elements or element combinations can be readily retrieved from the literature. Element combinations are understood here as element compounds such as, for example, water or plastics, solid compositions of bodies such as, for example, bones, or else known mixtures of individual elements. In each case, the absorption spectrum of this material is used in order to determine the concentration of the material inside the object to be examined.

The concentrations of the elements or element combinations in the object to be examined can therefore be determined with the aid of the present method at a specific location that is represented by the pixel in the X-ray image. A mean value on the path, represented by the pixel, of the X-radiation through the object to be examined is thereby obtained when use is made of a simple fluoroscopic method. In the preferred refinement of the present method, in which an X-ray-CT installation is used for recording the digital X-ray images, it is possible in this way to determine the concentration of the elements or element combinations for each volume element (voxel) of that region of the object to be examined which is being examined. Consequently, a spatial distribution of the concentrations of the chemical elements or element combinations, contained in the object to be examined, such as, for example, hydrogen, carbon or iron, is obtained by evaluating a plurality of pixels and X-ray tomographic images.

In the case of the examination of a human body as an object to be examined, this involves, in particular, the elements of nitrogen, carbon, oxygen, hydrogen and calcium. Again, the concentration of element combinations owing to the use of non-elementary absorption spectra such as, for example, those of water or bones, can be determined in this way in a spatially resolved fashion. Of course, the present method can be used not only in the field of medical technology, but also for numerous other technical applications, for example in the inspection of materials or in safety engineering. Here, the concentrations of the appropriate elements or element combinations of the respective object to be examined are then determined.

The basis of an embodiment of the present invention is that an attenuation coefficient μ of an element that is measured with the aid of an X-ray absorption method depends on the spectral apparatus function of the X-ray installation used, also denoted below as spectral weighting function w(E), and on the absorption spectrum κ(E) of the element:

$$\mu = \int \kappa(E) w(E) dE$$

a weighting function w(E) being obtained in the following way from the emitted X-ray spectrum S(E) and the spectral detector sensitivity D(E), where 0<D(E)<1:

$$w(E) = \frac{S(E)D(E)}{\int S(E)D(E)dE}$$

Given the preference of n different elements or element combinations, this relationship can be represented in the following way in matrix notation in the case of measurement of m attenuation values μ that are obtained with the various spectral distributions:

$$\begin{pmatrix} \mu 1 \\ \dots \\ \dots \\ \mu_m \end{pmatrix} = \mu_i = \sum_j^n c_j M_{ij}$$

where $$M_{ij} = \int_E w_i(E)\kappa_j(E)dE$$

This relationship can be used to determine a maximum of $n \leq m$ element concentrations from the measured data, $\mu_i$ corresponding to the m measured attenuation values $i=1$ to m, and $w_i$ corresponding to the spectral weighting function of the ith spectral measuring channel, that is to say the ith spectral distribution. $\kappa_j(E)$ represents the spectral absorption spectrum of the respective chemical element or the element combination that is known from the literature. In the matrix location illustrated, it is now possible to resolve in terms of the element concentrations or element combinations:

$$c_j = \sum_{i=1}^{m} M_{ij}^{-1}\mu_i.$$

$M_{ij}^{-1}$ is the inverse matrix of $M_{ij}$ and is calculated from the apparatus function, that is to say $w_i(E)$, of the X-ray installation.

In a preferred refinement of the present method, the concentration is calculated on the basis of this equation from the measured local attenuation values $\mu$. The different spectral distributions for the individual X-ray images, which correspond to the spectral weighting functions $w_i(E)$ of the X-ray installation, can be selected in this case such that the matrix $M_{ij}$ is as far as possible from the singularity ($M_{ij} \neq 0$), in order to permit an inversion of the matrix that is precise and stable against numerical errors. This can be implemented by including a K edge of an element to be determined in one of the spectral distributions or energy intervals, since this characteristic of the spectrum positively influences the invertibility of the matrix $M_{ij}$, and thus the accuracy of the determination of concentration.

An apparatus for carrying out the method in one embodiment includes in a known way at least one X-ray source for emitting X-radiation, and a number of X-ray detectors, situated opposite the X-ray source, for detecting X-ray attenuation data of an object to be examined arranged between the X-ray source and the X-ray detectors, as well as an evaluation unit for converting electric signals of the X-ray detectors into X-ray attenuation values. The apparatus is distinguished in that it includes a module for determining concentration that calculates the concentrations $c_j$ of the n elements and/or element combinations from m attenuation values for at least one pixel, representing the same location in a number of digital X-ray images of at least one region of the object to be examined, that were recorded with $m \geq n$ different spectral distributions of the X-radiation S(E) and/or the detector sensitivity D(E) under identical geometric conditions, taking account of known spectral absorption spectra $\kappa_j(E)$ of the n elements and/or element combinations and of the m different spectral distributions of the X-radiation S(E) and/or of the detector sensitivity D(E).

In one embodiment, the present method can be used particularly advantageously with an X-ray CT installation with the aid of which the spatially resolved images of the object to be examined are obtained. Novel three-dimensional information relating to the spatial concentration of chemical elements and/or element combinations in the object to be examined are obtained by using an embodiment of the present method in conjunction with computer tomography. The enhanced spectral resolution of existing or future X-ray absorption systems permits an accuracy sufficient for many applications.

BRIEF DESCRIPTION OF THE DRAWINGS

The present invention and the associated apparatus are further briefly explained below with the aid of an exemplary embodiment in conjunction with the drawings, in which.

DETAILED DESCRIPTION OF THE EXEMPLARY EMBODIMENTS

Figure 1:
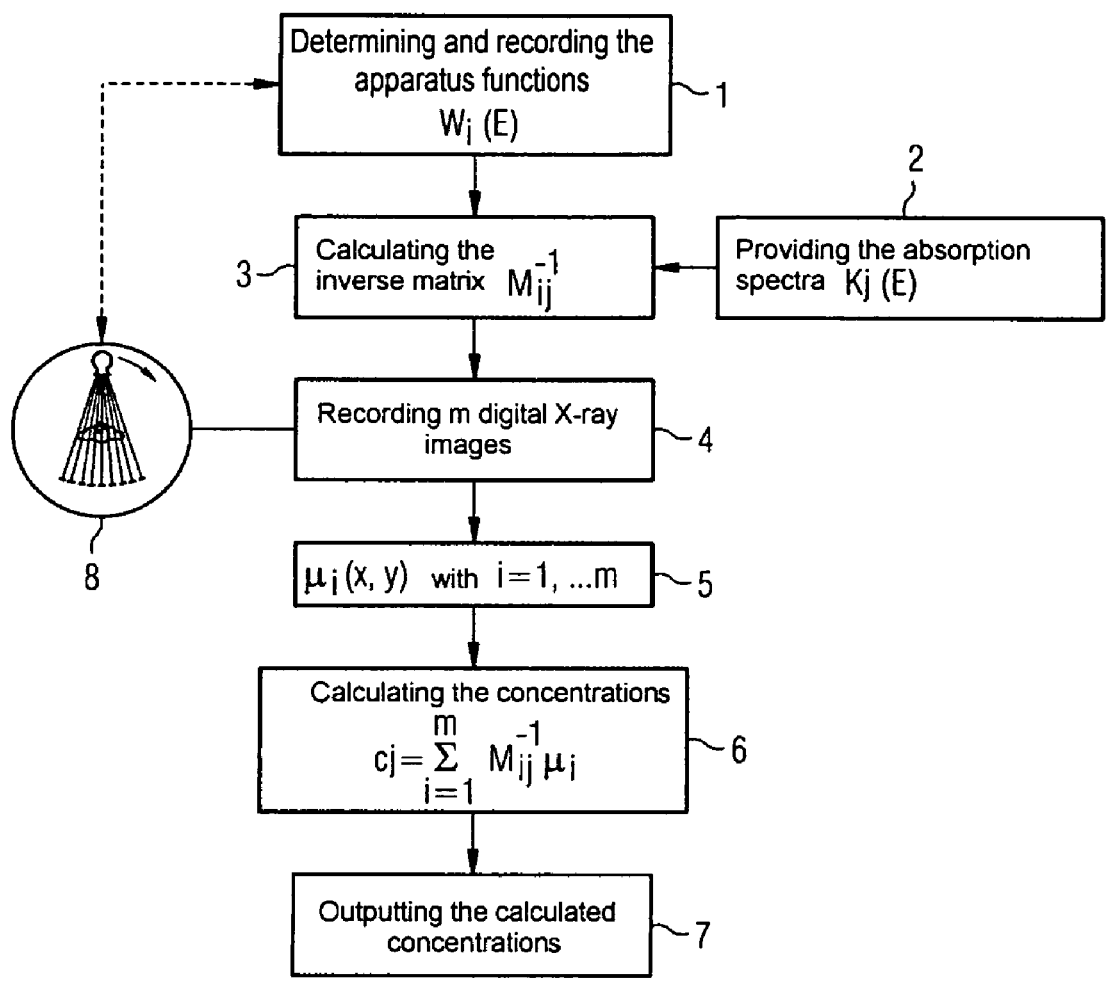
FIG. 1 shows a flowchart in accordance with an exemplary embodiment of the present method.

FIG. 1 shows a flowchart in accordance with an exemplary embodiment of the present method. The apparatus functions of the X-ray installation used, a computer tomograph 8 in the present example, are determined and recorded in the first step 1 in this method. These apparatus functions $w_i(E)$ are composed of the spectral distribution emitted by the X-ray source, of the input intensity S(E) and the spectral detector sensitivity D(E). Both the X-ray spectrum S(E) and the detector sensitivity D(E) can be subdivided into spectral regions for the purpose of producing the various spectral distributions for the individual X-ray images.

The inverse matrix $M_{ij}^{-1}$ is calculated in step 3 after the determination and recording of the apparatus functions $w_i(E)$. The known absorption spectra of the elements and/or element combinations of which the region of the object to be examined consists are prepared (step 2) for this purpose. In the case of a human object to be examined, these are, for example, the absorption spectra of the elements hydrogen, carbon, nitrogen, oxygen and calcium.

After the calculation of the inverse matrix, the object to be examined is examined in step 4 in the X-ray computer tomography 8 likewise indicated here, in order to obtain m digital X-ray pictures that are recorded in conjunction with the m different apparatus functions previously defined.

The image reconstruction required in computer tomography is carried out in step 5 on the basis of the raw data obtained from the detectors; in this image reconstruction, the attenuation value distribution $\mu_i(x, y)$, where $i=1$ to m, inside a transverse tomogram with the coordinates x and y is produced for each of the X-ray images.

Finally, in step 6 the concentrations $c_j$ are calculated by way of $$c_j = \sum_{i=1}^{m} M_{ij}^{-1}\mu_i$$

from the attenuation values $\mu_i(x, y)$, this being done for at least one pixel, that is to say one location $x_0$, $y_0$ from the associated attenuation values $\mu_i(x_0, y_0)$.

In the case of the present example, this calculation is carried out for all pixels and tomograms of the region of interest, and so a spatial concentration distribution of the elements or element combinations of which the object to be examined is composed is obtained. The correspondingly calculated concentrations are output in step 7 on an appropriate monitor. This output can also be performed, for example, in a graphic display, in which case the display can be done element by element, for example, that is to say an image that displays the concentration distributions of the element in this region is output for each element and section of the object to be examined. In another refinement, it is also possible to implement an interaction in which the operator sees an appropriately selected transverse tomogram on the monitor in the usual way and, by clicking on a pixel or region of the image inside the transverse tomogram, for example with the aid of a mouse pointer via a graphics user interface, prompts the display of information relating to the element concentrations determined in this region.

Figure 2:
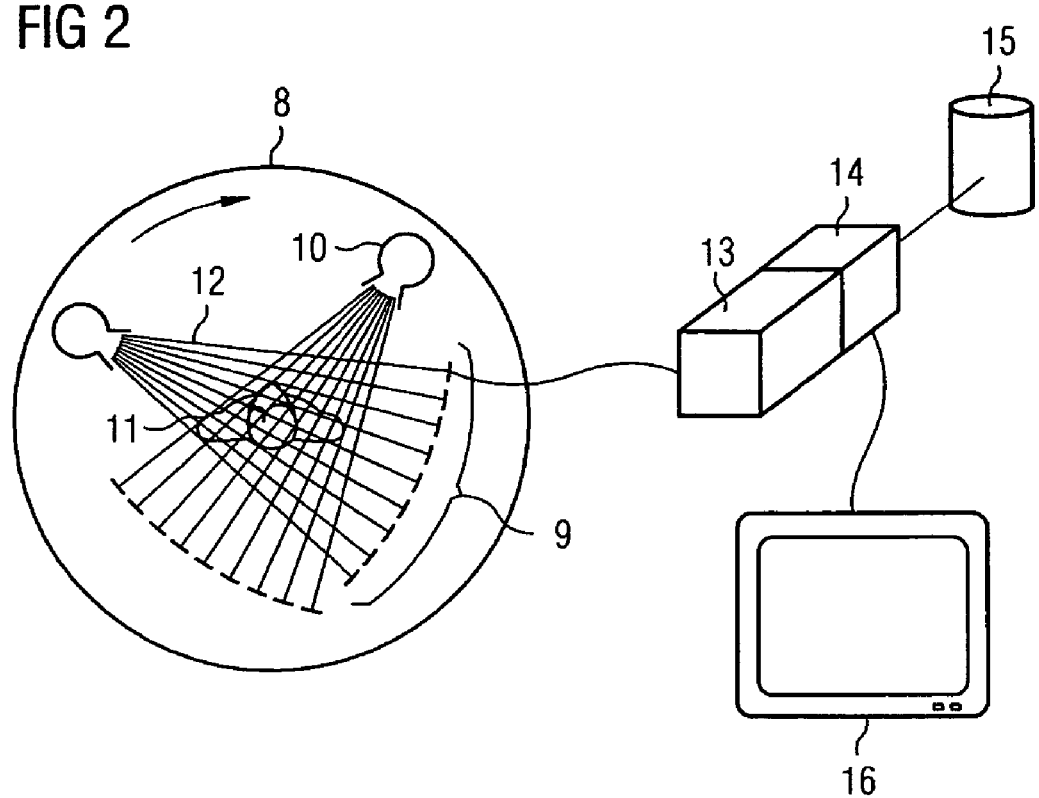
FIG. 2 shows a diagram of an example for the design of the present apparatus.

Finally, FIG. 2 shows a highly schematic example for the design of the present apparatus. An X-ray CT unit 8 with a rotating detector system 9 is to be seen in this figure. The X-rays 11 emitted in the shape of a fan by the X-ray tubes 10 transluminate the object 12 to be examined from a specific angular position, and finally strike a linear arrangement of discrete detectors. A recording cycle includes a multiplicity of such transluminations at different angular positions relative to the object to be examined. The electric signals supplied by the X-ray detectors 9 are converted into X-ray attenuation values by an evaluation unit 13.

In the present example, this evaluation unit 13 includes a module 14 for determining concentration that calculates the concentrations $c_j$ of the n elements and/or element combinations from m attenuation values for at least one pixel, representing the same location in a number of digital X-ray images of at least one region of the object to be examined, that were recorded with m≧n different spectral distributions of the X-radiation S(E) and/or the detector sensitivity D(E) under identical geometric conditions, taking account of known spectral absorption spectra $\kappa_j(E)$ of the n elements and/or element combinations and of the m different spectral distributions of the X-radiation S(E) and/or of the detector sensitivity D(E). The spectral absorption spectra $\kappa_j(E)$ of the n elements and/or element combinations are stored in this example in the storage device 15 from which they are retrieved by the module 14.

The result is displayed on the connected monitor 16.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the spatially-resolved determination of the concentration of at least one of n elements and element combinations in an object to be examined that is composed of at least one of n elements and element combinations, the method comprising:
   using an X-ray installation to record, at least one of simultaneously and sequentially under the same geometric conditions, a number of digital X-ray images of at least one region of the object to be examined with the aid of m≧n different spectral distributions of at least one of the X-radiation S(E) and of the detector sensitivity D(E), in order to obtain m attenuation values μi for each pixel representing the same location in the X-ray images; and
   calculating the concentrations of the at least one of n elements and element combinations for at least one pixel from the respective m attenuation values μI, while taking account of known spectral absorption spectra $K_j(E)$ of the at least one of n elements and element combinations and of the m different spectral distributions of at least one of the X-radiation S(E) and of the detector sensitivity D(E), wherein the concentrations $c_j$ of at least one of the n elements and element combinations are calculated using the following formula:

$$c_j = \sum_i^m \mu_i M_{ij}^{-1},$$

where $$M_{ij} = \int_E w_i(E) K_j(E) dE$$

and $w_i$ represents a spectral weighting function for the ith spectral distribution, which is given by $$w(E) = \frac{S(E)D(E)}{\int S(E)D(E)dE}.$$

2. The method as claimed in claim 1, wherein the digital X-ray images are recorded with m spectral distributions of the detector sensitivity D(E), which represent an at least approximately uniform subdivision of the X-ray spectrum of the X-radiation emitted by the X-ray installation.

3. The method as claimed in claim 2, wherein the spectral distributions are selected such that at least one K edge of one of at least one of the n elements and element combinations falls into one of the spectral distributions.

4. The method as claimed in claim 2, wherein the X-ray images are recorded with the aid of an X-ray-CT installation.

5. The method as claimed in claim 1, wherein the spectral distributions are selected such that at least one K edge of one of at least one of the n elements and element combinations falls into one of the spectral distributions.

6. The method as claimed in claim 5, wherein the X-ray images are recorded with the aid of an X-ray-CT installation.

7. The method as claimed in claim 1, wherein the X-ray images are recorded with the aid of an X-ray-CT installation.

8. The method as claimed in claim 1, wherein the digital X-ray images are recorded with m spectral distributions of the detector sensitivity D(E), which represent an at least approximately uniform subdivision of the X-ray spectrum of the X-radiation emitted by the X-ray installation.

9. The method as claimed in claim 1, wherein the spectral distributions are selected such that at least one K edge of one of at least one of the n elements and element combinations falls into one of the spectral distributions.

10. The method as claimed in claim 1, wherein the X-ray images are recorded with the aid of an X-ray-CT installation.

11. An apparatus for the spatially-resolved determination of the concentration of at least one of n elements and element combinations in an object to be examined, comprising:
    an X-ray source for emitting X-radiation;
    a plurality of X-ray detectors, situated opposite the X-ray source, for the spatially-resolved detection of impinging X-radiation; and
    an evaluation unit for convening electric signals of the X-ray detectors into attenuation values, wherein the evaluation unit includes a module for determining concentration which calculates the concentrations of at least one of the n elements and element combinations from m attenuation values for at least one pixel representing the same location in a number of digital X-ray images of at least one region of the object to be examined, which were recorded with the aid of m≧n different spectral distributions of at least one of the X-radiation S(E) and of the detector sensitivity D(E) under the same geometric conditions, taking account of known spectral absorption spectra of at least one of the n elements and element combinations and of the m different spectral distributions of at least one of the X-radiation S(E) and detector sensitivity D(E), wherein the concentrations $c_j$ of at least one of the n elements and element combinations are calculated using the following formula:

$$c_j = \sum_i^m \mu_i M_{ij}^{-1},$$

where $$M_{ij} = \int_E w_i(E) K_j(E) dE$$

and $w_i$ represents a spectral weighting function for the ith spectral distribution, which is given by $$w(E) = \frac{S(E)D(E)}{\int S(E)D(E)dE}.$$

12. The apparatus as claimed in claim 11, wherein the digital X-ray images are recorded with m spectral distributions of the detector sensitivity D(E), which represent an at least approximately uniform subdivision of the X-ray spectrum of the X-radiation emitted by the X-ray installation.

13. The apparatus as claimed in claim 11, wherein the spectral distributions are selected such that at least one K edge of one of at least one of the n elements and element combinations falls into one of the spectral distributions.

14. The apparatus as claimed in claim 11, wherein the X-ray images are recorded with the aid of an X-ray-CT installation.

15. An apparatus for determining the concentration of at least one of n elements and element combinations in an object to be examined that is composed of at least one of n elements and element combinations, the apparatus comprising:

means for recording a plurality of digital X-ray images of at least one region of the object to be examined with the aid of m≧n different spectral distributions of at least one of the X-radiation and detector sensitivity, to obtain m attenuation values for each pixel representing the same location in the X-ray images; and means for calculating the concentrations of the at least one of n elements and element combinations for at least one pixel from the respective m attenuation values, while taking account of known spectral absorption spectra of the at least one of n elements and element combinations and of the m different spectral distributions of at least one of the X-radiation and of the detector sensitivity, wherein the concentrations $c_j$ of at least one of the n elements and element combinations are calculated using the following formula:

$$c_j = \sum_i^m \mu_i M_{ij}^{-1},$$

where $$M_{ij} = \int_E w_i(E) K_j(E) dE$$

and $w_i$ represents a spectral weighting function for the ith spectral distribution, which is given by $$w(E) = \frac{S(E)D(E)}{\int S(E)D(E)dE}.$$

16. The apparatus as claimed in claim 15, wherein the digital X-ray images are recorded with m spectral distributions of the detector sensitivity D(E), which represent an at least approximately uniform subdivision of the X-ray spectrum of the X-radiation emitted by the X-ray installation.

17. The apparatus as claimed in claim 15, wherein the spectral distributions are selected such that at least one K edge of one of at least one of the n elements and element combinations falls into one of the spectral distributions.

18. The apparatus as claimed in claim 15, wherein the X-ray images are recorded with the aid of an X-ray-CT installation.

* * * * *